US008119638B2

(12) United States Patent
Cvitkovich et al.

(10) Patent No.: US 8,119,638 B2
(45) Date of Patent: Feb. 21, 2012

(54) COMPOSITIONS AND USES OF ET743 FOR TREATING CANCER

(75) Inventors: Esteban Cvitkovich, Paris (FR); George Daniel Demetri, Boston, MA (US); Cecilia Guzman, Madrid (ES); Jose Jimeno, Madrid (ES); Luis Lopez Lazaro, Madrid (ES); Jean Louis Misset, Villejuif Cedex (FR); Chris Twelves, Glasgow (GB); Daniel D. Von Hoff, Tuscon, AZ (US)

(73) Assignee: Pharma Mar, S.A. (ES)

( * ) Notice: Subject to any disclaimer, the term of this patent is extended or adjusted under 35 U.S.C. 154(b) by 149 days.

(21) Appl. No.: 11/769,873

(22) Filed: Jun. 28, 2007

(65) Prior Publication Data

US 2007/0275942 A1 Nov. 29, 2007

(51) Int. Cl.
A61K 31/495 (2006.01)
A61K 31/56 (2006.01)
(52) U.S. Cl. ........................................ 514/250; 514/171
(58) Field of Classification Search .................. 514/171, 514/250
See application file for complete search history.

(56) References Cited

U.S. PATENT DOCUMENTS

| 5,089,273 | A | 2/1992 | Rinehart et al. |
| 5,149,804 | A | 9/1992 | Rinehart et al. |
| 5,256,663 | A | 10/1993 | Rinehart et al. |
| 5,478,932 | A | 12/1995 | Rinehart et al. |
| 5,552,544 | A | 9/1996 | Brana et al. |
| 5,654,426 | A | 8/1997 | Rinehart et al. |
| 5,721,362 | A | 2/1998 | Corey et al. |
| 5,908,835 | A | 6/1999 | Bissery |
| 5,985,876 | A | 11/1999 | Rinehart et al. |
| 6,124,293 | A | 9/2000 | Rinehart et al. |
| 6,153,590 | A | 11/2000 | Andersen et al. |
| 6,348,467 | B1 | 2/2002 | Corey |
| 7,241,892 | B1 | 7/2007 | Cuevas et al. |
| 7,247,892 | B2 | 7/2007 | Taylor et al. |
| 7,410,969 | B2 | 8/2008 | Manzanares et al. |
| 7,420,051 | B2 | 9/2008 | Francesch |
| 7,524,956 | B2 | 4/2009 | Cuevas |
| 7,622,458 | B2 | 11/2009 | Rybak et al. |
| 2002/0137663 | A1 | 9/2002 | Forman et al. |
| 2004/0002602 | A1 | 1/2004 | Francesch et al. |
| 2004/0019027 | A1 | 1/2004 | Forman et al. |
| 2004/0108086 | A1 | 6/2004 | Takahashi et al. |
| 2005/0004018 | A1 | 1/2005 | Jimeno |
| 2006/0030571 | A1 | 2/2006 | Rinehart |
| 2006/0094687 | A1 | 5/2006 | Beijnen |
| 2007/0004691 | A1 | 1/2007 | Donald |
| 2007/0082856 | A1 | 4/2007 | Gianni |
| 2007/0128201 | A1 | 6/2007 | D'Incalci et al. |
| 2007/0275942 | A1 | 11/2007 | Cvitkovich |
| 2008/0076772 | A1 | 3/2008 | Allavena |
| 2008/0255132 | A1 | 10/2008 | Rowinsky |
| 2008/0293725 | A1 | 11/2008 | Rosell Costa |
| 2009/0117176 | A1 | 5/2009 | Gilles |
| 2009/0170860 | A1 | 7/2009 | Scotto |
| 2009/0324744 | A1 | 12/2009 | Takahashi |
| 2010/0009906 | A1 | 1/2010 | Ali Elsayed |

FOREIGN PATENT DOCUMENTS

| CN | 1486193 | 3/2004 |
| WO | WO 99/51238 | 10/1999 |
| WO | WO 99/58125 | 11/1999 |
| WO | WO 00/69441 | 11/2000 |
| WO | WO 00/69862 | 11/2000 |
| WO | WO 01/77115 | 10/2001 |
| WO | WO 01/87894 | 11/2001 |
| WO | WO 02/36135 | 5/2002 |
| WO | WO 02/064843 | 8/2002 |
| WO | WO 02/078678 | 10/2002 |
| WO | WO 03/020259 | 3/2003 |
| WO | WO 03/039571 | 5/2003 |
| WO | WO 2005/049029 | 6/2005 |
| WO | WO 2005/049030 | 6/2005 |
| WO | WO 2005/049031 | 6/2005 |
| WO | WO 2006/035244 | 4/2006 |
| WO | WO 2006/046080 | 5/2006 |

OTHER PUBLICATIONS

Akers, "Excipient—Drug Interactions in Parenteral Formulations," Journal of Pharmaceutical Sciences, 91(11), pp. 2283-2300, Nov. 2002.

Barrera, H. et al., "Interaction of ET-743 and standard cytotoxic agents against a panel of human tumor cell lines," Proceedings of the American Association for Cancer Research, vol. 40, p. 591, Abstract No. 3896, Mar. 1999.

Biroccio et al., "Telomere Dysfunction Increases Cisplatin and Ecteinascidin-743 Sensitivity of Melanoma Cells," Molecular Pharmacology, 63:632-638 (2003).

Blay et al., "Combination of Trabectedin and Doxorubicin for the Treatment of Patients with Soft Tissue Sarcoma: Safety and Efficacy Analysis," 43rd annual ASCO meeting, Jun. 1-5, 2007.

Bonfanti et al., "Effect of Ecteinascidin-743 on the Interaction Between DNA Binding Proteins and DNA." Anticancer Drug Des. 14, 179-86, 1999.

Bowman, A. et al., "Phase I clinical and pharmacokinetic (PK) study of ecteinascidin-743 (ET-743) given as a one hour infusion every 21 days," Annals oncology, Abstract 452, 1998.

Brandon et al., In-vitro Cytotoxicity of ET-743 (Trabectedin, Yondelis), a Marine Anti-cancer Drug, in the Hep G2 Cell Line: Influence of Cytochrome P450 and Phase II Inhibition, and Cytochrome P450 Induction, Anti-cancer Drugs, 16:935-943 (2005).

(Continued)

Primary Examiner — James D Anderson
(74) Attorney, Agent, or Firm — Kenneth H. Sonnenfeld; King & Spalding

(57) ABSTRACT

Et 743 is used in the preparation of a medicament for the treatment of the human body for cancer.

13 Claims, 1 Drawing Sheet

OTHER PUBLICATIONS

Burstein et al., "Phase I study of Doxil and Vinorelbine in Metastatic Breast Cancer," Annals of Oncology, vol. 10, pp. 1113-1116, 1999, XP8086751.

European Agency for the Evaluation of Medicinal Products, "Committee for Proprietary Medicinal Products Summary of Opinion for Yondelis", Nov. 20, 2003.

Corey et al., "Enantioselective Total Synthesis of Ecteinascidin 743", J. Am. Chem. Soc., 118, 9202-9203, 1996.

Cvitkovic, E. et al., "Final results of a phase I study of ecteinascidin-743 (ET-743) 24 hour (h) continuous infusion (CI) in advanced solid tumors (AST) patients (pts)," 1999 ASCO Annual Meeting Proceedings, Abstract No. 690, May 15-18, 1999.

Cvitkovic, E. et al., "Ecteinascidin-743 (ET-743) 24 hour continuous intravenous infusion (CI) phase I study in solid tumors (ST) patients," Annals Oncology, Abstract 456, 1998.

Delaloge et al., "Ecteinascidin (ET-743) in heavily pretreated refractory sarcomas: Preliminary evidence of activity," Eur. J. Cancer, vol. 35, suppl. 4, p. S271, Abstract No. 1080, Sep. 15, 1999.

Delaloge, S. et al., "Ecteinascidin-743: A Marine-Derived Compound in Advanced Pretreated Sarcoma Patients—Preliminary Evidence of Activity", J. of Clinical Oncology, vol. 19, No. 5, pp. 1248-1255, 2001.

DeVita et al., "Combination Versus Single Agent Chemotherapy: A Review of the Basis for Selection of Drug Treatment of Cancer", Cancer, vol. 35, pp. 98-110, 1975.

D'Incalci et al., "Mode of action of Ecteinascidin-743 (ET-743)," Proceedings of the 1999 AACR-NCI-EORTC International Conference, Clinical Cancer Research, vol. 5, Supplement, pp. 3872s-3873s, Abstract of Plenary Session 7, Nov. 16-19, 1999.

D'Incalci et al., "The Combination of ET-743 and Cisplatin (DDP): From a Molecular Pharmacology Study to a Phase I Clinical Trial," from the AACR Annual Meeting of Apr. 6-10, 2002, Abstract 404.

D'Incalci et al., "In human tumor xenografts the resistance to ET-743 or to cisplatin can be overcome by giving the two drugs in combination," European Journal of Cancer, 38, Suppl. 7, 34 (Nov. 2002).

D'Incalci et al., "Preclinical and Clinical Results with the Natural Marine Product ET-743," Expert Opin. Investig. Drugs, 12(11):1843-1853 (2003).

D'Incalci et al., "The combination of yondelis and cisplatin is synergistic against human tumor xenografts," European Journal of Cancer 39: 1920-1926 (2003).

Donald et al., "Complete Protection by High-Dose Dexamethasone Against The Hepatotoxicity of the Novel Antitumor Drug Yondelis (ET-743) in The Rat," Cancer Research, vol. 63, p. 5902-5908, Sep. 2003.

Donald et al., "Dietary Agent Indole-3-Carbinol Protects Female Rats Against the Hepatotoxicity of the Antitumor Drug ET-743 (trabectidin) Without Compromising Efficacy in a Rat Mammary Carcinoma" International Journal of Cancer, vol. 111, No. 6, p. 961-967, 2004.

Dorr and Van Hoff, "Doxorubicin," Cancer Chemotherapy Handbook, 1994, pp. 395-416.

"Doxil (doxorubicin HCl Liposome Injection) Product Information", Oct. 10, 2004, pp. 1-16, XP002389462, <<web.archive.org/web/20041009180>>.

Drugs Fut., "Ecteinascidin-743" vol. 22, No. 11, p. 1279, 1997.

Eckhardt et al., "In vitro Studies of a Novel Marine Cytotoxic, Ecteinascidin (ET-743)," New Drugs and Pharmacology, Annals of Oncology, 7 (Suppl. 5), 131, Abstract 632P (1996).

Endo et al., "Total Synthesis of Ecteinascidin 743", J. Am. Chem. Soc., 124, 6552-6554, 2002.

Erba et al., "Synergistic cytotoxic effect of ET-743 and cisplatin," Clinical Cancer Research, vol. 6, Abstract 209, Nov. 7-10, 2000.

Erba et al., "Combination of yondelis (ET-743) and oxaliplatin in experimental ovarian cancer," from the AACR-NCI-EORTC International Conference on Molecular Targets and Cancer Therapeutics of Nov. 17-21, 2003, Abstract C247.

Erba et al., "ET-743 and Cisplatin (DDP) Show in Vitro and in Vivo Synergy Against Human Sarcoma and Ovarian Carcinoma Cell Lines," from the AACR-NCI-EORTC Conference on Molecular Targets and Cancer Therapeutics of Oct. 29-Nov. 2, 2001, Abstract 406.

Erlichman, C., "18: Pharmacology of Anticancer Drugs," The Basic Science of Oncology, 2nd edition, Tannock et al., editors, McGraw-Hill, New York, pp. 317-337, 1992.

FDA approved label for Pharmacia and Upjohn's Doxorubicin Hydrochloride for Injection (May 8, 2003).

Faircloth et al., "In Vivo Combinations of Chemotherapeutic Agents with Ecteinascidin 743 (ET743) Against Solid Tumors," from the Proceedings AACR-NCI-EORTC of Nov. 2001, Abstract 387.

Faircloth et al., "Dexamethasone Potentiates the Activity of Ecteinascidin 743 in Preclinical Melanoma and Osteosarcoma Models," Abstract and Presentation 379 (2002).

Faulkner et al., "Symbiotic Bacteria in Sponges: Sources of Bioactive Substances," Drugs from the Sea, Fusetani, N. (ed.), Basel Karger, 2000, pp. 107-119.

Fayette et al., "ET-743: a Novel Agent with Activity in Soft-Tissue Sarcomas," Current Opinion in Oncology, 18:347-353 (2006).

Fourouzesh, B. et al., "Phase I and pharmacokinetic study of the marine-derived DNA minor groove binder ET-743 on a weekly x3 every-4-week schedule in patients with advanced solid malignancies," Proceedings of the 2001 AACR-NCI-EOTRC International Conference, Abstract No. 209, Oct. 29-Nov. 2, 2001.

Fourouzesh, B. et al., "Phase I and pharmacokinetic study of ET-743, a minor groove DNA binder, administrated weekly to patients with advanced cancer," Proc Am Soc Clin Oncol, vol. 20, 2001 ASCO Annual Meeting Proceedings, Abstract No. 373, 2001.

Forouzesh, B., et al., "Phase I and pharmacokinetic study of ET-743, a minor groove DNA binder, administered weekly to patients with advanced cancer," European Journal of Cancer, ECCO 11, vol. 37, supplement 6, Abstract No. 106, Oct. 21-25, 2001.

Friereich et al., "Quantitative Comparison of Toxicity of Anticancer Agents in Mouse, Rat, Hamster, Dog, Monkey, and Man," Cancer Chemotherapy Reports, 50:4, May 1966, pp. 219-245.

Fukuyama et al., "Total Synthesis of Saframycin A," J. Am. Chem. Soc., 112, 3712-3713, 1990.*

Fukuyama et al., "Stereocontrolled Total Synthesis of Saframycin B," J. Am. Chem. Soc., 104, 4957-4958, 1982.*

Garcia-Carbonero et al., "Population pharmacokinetics of ecteinascidin 743 in patients with advanced soft tissue sarcoma," Clinical Cancer Research, vol. 6, Supplement, Abstract 211, p. 4508s, NCI-EORTC-AACR Symposium on New Drugs in Cancer Therapy, Nov. 7-10, 2000.*

Garcia Gravalos, M.D., et al., "In vitro schedule-dependent cytotoxicity by ecteinascidin 743 (ET-743) against human tumor cells," 23rd European Society for Medical Oncology Congress, Abstract No. 652, Nov. 6-10, 1998.*

Ghielmini, M. et al., "Schedule-dependent myelotoxicity induced in vitro by the new marine derived minor groove interacting agent ecteinascidin 743," ECCO, vol. 9, Abstract No. 807, Sep. 17, 1997.*

Ghielmini, M. et al., "In vitro schedule-dependency of myelotoxicity and cytotoxicity of Ecteinascidin 743 (ET-743)," Annals of Oncology, vol. 9, pp. 989-993, 1998.*

Gianni et al. "Definition of the Least Toxic Sequence and Optimal Therapeutic Dose of Yondelis® in Combination with Doxorubicin in Patients with Untreated Metastatic Soft Tissue Sarcomas and Advanced Pre-Treated Anthracycline," Clinical Cancer Research, vol. 9, No. 16, p. 6081S (Dec. 2003).*

Giovanna et al., "Importance of DNA repair mechanisms for the sensitivity of tumor cells to ET-743," Proceedings of the 1999 AACR-NCI-EORTC International Conference, Clinical Cancer Research, vol. 5, Supplement, p. 3790s, Abstract 303, Nov. 16-19, 1999.*

Goodman & Gilman's The Pharmaceutical Basis of Therapeutics, p. 36, 1975.*

Goodman & Gilman's The Pharmaceutical Basis of Therapeutics (9$^{th}$ edition), p. 930, 1996.*

Goodman & Gilman's The Pharmaceutical Basis of Therapeutics (9$^{th}$ edition), pp. 1230. 1232, 1996.*

Gore et al., "Phase I Combination Study of Trabectedin and Capecitabine in Patients With Advanced Malignancies," Poster Presentation, 42nd ASCO Annual Meeting held on Jun. 2-6, 2006, Atlanta, Georgia.*

Grever et al., "The National Cancer Institute: Cancer Drug Discovery and Development Program", Seminars in Oncology, vol. 19, No. 6, 622-638, Dec. 1992.*

Grosso et al., "Steroid Premedication Markedly Reduces Liver and Bone Marrow Toxicity of Trabectedin in Advanced Sarcoma," European Journal of Cancer 42:10, 1484-1490 (2006).

Gurtler, J.S. et al., "Trabectedin in third line breast cancer: a multicenter, randomized, phase II study comparing two administration regimens," Journal of Clinical Oncology, 2005 ASCO Annual Meeting Proceedings, vol. 23, No. 16S, part I of II (Jun. 1 Supplement), Abstract No. 625, 2005.

Hendriks, H.R. et al., "High antitumor activity of ET743 against human tumor xenografts from melanoma, non-small-cell lung and ovarian cancer," Annals of Oncology, vol. 10, pp. 1233-1240, 1999.

Hidalgo, M., et al., "A phase I and pharmacokinetic (PK) study of ET-743, a novel minor groove binder of marine origin administered on a daily × 5 schedule," 23rd European Society for Medical Oncology Congress, Abstract No. 613P, Nov. 6-10, 1998.

Hillebrand, M.J.X. et al., "Pharmacokinetics of ecteinascidin-743 (ET-743) in three phase I studies," Annals Oncology, Abstract No. 455, 1998.

Holmes, "Paclitaxel Combination Therapy in the treatment of Metast Breast Cancer: A Review," Seminars in Oncology, vol. 23, pp. 46-56, 1996.

Hornicek et al., "In vitro effect of the tetrahydroisoquinoline alkaloid Ecteinascidin-743 (ET-743) on chondrosarcoma (CHSA) cells," Proceedings of the 1999 AACR-NCI-EORTC International Conference, Clinical Cancer Research, vol. 5, Supplement, p. 3790s, Abstract 304, Nov. 16-19, 1999.

Hornicek et al., "Effect of Ecteinascidin-743 and Plasminogen related Protein B on a Human Chondrosarcoma Xenograft Tumor in Mice," Clinical Cancer Research, vol. 7 Supplement P3734S-3734S, Abstract 398 (Nov. 2001).

Ishikawa et al., "Tumor Selective Delivery of 5-Fluorouracil by Capecitabine," Biochemical Pharmacology, vol. 55, pp. 1091-1097, 1998.

Izbicka, E. et al., "In vitro antitumor activity of the novel marine agent, Ecteinascidin-743 (ET-743, NSC—648766) against human tumors explanted from patients," Annals of Oncology, vol. 9, pp. 981-987, 1998.

Jimeno, J.M. et al., "Enhancing the preclinical in vivo antitumor activity of ecteinascidin 743, a marine natural product currently in phase II clinical trials," Proceedings of the 1999 AACR-NCI-EORTC International Conference, Clinical Cancer Research, vol. 5, p. 3790S, Abstract No. 306, Nov. 16-19, 1999.

Jimeno et al., "Pharmacokinetics (PK)/Pharmacodynamic (PD) Relationships in Patients (PT) Treated With Ecteinascidin-743 (ET-743) Given As 24 Hours Continuous Infusion (CI)," Journal of Clinical Oncology, ASCO Annual Meeting Proceedings, Abstract No. 744, May 15-18, 1999.

Jimeno, J. et al., "Phase I and pharmacokinetic (PK) study of Et-743, a novel minor groove binder of marine origin on a daily [times] 5 schedule," 1998 ASCO Annual Meeting Proceedings, Abstract No. 737, 1998.

Jimeno, Jose et al., "Adding Pharmacogenomics to the Development of New Marine-Derived Anticancer Agents," Journal of Translational Medicine, vol. 4, issue 3, Jan. 9, 2006, downloaded from the internet website: <<http://www.translational-medicine.com/content/4/1/3>>.

Jin et al., "The antitumor agent Ecteinascidin 743 (ET743), inhibits transcriptional activation of the MDR1 Gene by multiple inducers," Proceedings of the 1999 AACR-NCI-EORTC International Conference, Clinical Cancer Research, vol. 5, Supplement, p. 3790s, Abstract 302, Nov. 16-19, 1999.

Jin et al., Ecteinascidin-743, A Transcription-Targeted Chemotherapeutic that Inhibits MDR I Activation. Proc. Natl. Acad. Sci. USA, 97, 6775-9, 2000.

Kanzaki et al., "Activity of Ecteinascidin 743 and Synergism with Doxorubicin and Vincristine in P-Glycoprotein/MDR1 Over-Expression Cell Lines," from the Proceedings of the AACR, vol. 42, Abstract 4354 (Mar. 2001).

Kanzaki et al., "Microsatellite Instability (MSI) Induced by Ecteinascidin743 and Protection with Aspirin," from the 93rd Annual Meeting of the American Association for Cancer Research, Abstract 5382 (Apr. 6-10, 2002), vol. 43, Mar. 2002, p. 1087.

Kovalcik et al., "The Stability of Cyclophosphamide in Lyophilized Cakes. part I. Mannitol, Lactose, and Sodium Biocarbonate as Excipients," Journal of Parenteral Science and Technology, vol. 42, No. 1, Jan.-Feb. 1988, pp. 29-37.

Laverdiere et al., "Phase II Study of Ecteinascidin 743 in Heavily Pretreated Patients with Recurrent Osteosarcoma", Cancer, American Cancer Society, Philadelphia, PA, Aug. 15, 2003, vol. 98:4, pp. 832-840, XP002314512.

Leonetti et al., "Antitumoral Effect of the G-quadraplex Interactive Compound RHPS4 on Human Melanoma Cells Possessing Relatively Long Telomeres," from the Proceedings of the AACR, vol. 45, Mar. 2004.

Lopez-Lazaro et al., "Exploratory evaluation of the potential predictors for dose-limiting toxicities (DLTs) in patients treated with Ecteinascidin-743 (ET-743) as a 24-h intravenous (iv) infusion every 3 weeks and its relationship to pharmacokinetics (PK)," Proceedings of the 1999 AACR-NCI-EORTC International Conference, Clinical Cancer Research, vol. 5, Supplement, p. 3791s, Abstract 308, Nov. 16-19, 1999.

Lyass et al., "Phase I Study of Doxil-Cisplatin Combination Chemotherapy in Patients with Advanced Malignancies," Clinical Cancer Research, vol. 7, pp. 3040-3046, Oct. 2001, XP8086753.

Maier et al., "In vitro inhibition of endothelial cell growth by the antiangiogenic drug AGM-1470 (TNP-470) and the antiendoglin antibody TEC-11," Anti-Cancer Drugs, vol. 8, pp. 238-244, 1997.

Magro et al., "The Role of PARP and PARP Inhibitors in Yondelis (Trabectedin) Mediated Cytotoxicity," Abstract and Presentation from the AACR Annual Meeting, Apr. 17, 2007.

Manzanares et al., "Advances in the Chemistry and Pharmacology of Ecteinascidins, A Promising New Class of Anticancer Agents," Curr. Med. Chem.—Anti-Cancer Agents, 2001, vol. 1, pp. 257-276.

Martinez et al., "Phthalascidin, A Synthetic Antitumor Agent with Potency and Mode of Action Comparable to Eeteinaseidin 743." Proc. Natl. Acad. Sci. USA 96; 3496-501, 1999.

Martinez, E. J. et al., "A New, More Efficient, and Effective Process for the Synthesis of a Key Pentacyclic Intermediate for Production of Ecteinascidin and Phthalascidin Antitumor Agents." Org. Lett. 2, 993-6, 2000.

McLeod, "Clinically relevant drug-drug interactions in oncology," Br. J. Clin. Pharmacol., 45:539-544 (1998).

McMeekin, D.S. et al., "Final results of a phase II study of weekly trabectedin in second/third line ovarian carcinoma," Journal of Clinical Oncology, 2005 ASCO Annual Meeting proceedings, vol. 23, No. 16S, Part I of II (Jun. 1 Supplement), Abstract No. 5011, May 13-15, 2005.

Meco et al., "Effective combination of ET-743 and doxorubicin in sarcoma: preclinical studies," Cancer Chemother. Pharmacol. 52: 131-138 (2003).

Meco et al., "The combination of ET-743 and Irinotecan is active in preclinical models in rhabomyosarcoma," presented at the 16th EORTC-NCI-AARC Symposium on Molecular Targets and Cancer Therapeutics held in Geneva on Sep. 28-Oct. 1, 2004.

Menchaca et al., "Synthesis of Natural Ecteinascidins (ET-729, ET-745, ET-759B, ET-736, ET-637, ET-594) from Cyanosafracin B," J. Org. Chem., published on web Oct. 21, 2003, pp. 8859-8866.

Merck Manual on-line edition version, "Types: Overview of Cancer," 4 pages, downloaded from internet website <<http://www.merck.com/mmhe>>, Feb. 2003.

Michaelson, M.D. et al., "Phase II study of three hour, weekly infusion of trabectedin (ET-743) in men with metastatic, androgen-independent prostatecarcinoma (AIPC)," Journal of Clinical Oncology, 2005 ASCO Annual Meeting Proceedings, vol. 23, No. 16S, Part I of II (Jun. 1 Supplement), Abstract No. 4517, May 13-17, 2005.

Minuzzo, M. et al., "Interference of Transcriptional Activation by the Antineoplastic Drug Ecteinascidin.743." Proc. Natl. Acad. Sci. USA 97, 6780-4, 2000.

Moore et al., "Sequencing evaluation of ET-743 combinations with standard chemotherapy agents against a panel of human tumor cell lines," Clinical Cancer Research, vol. 6, Abstract 504 (Nov. 2000).

Morioka et al., "Antiangiogenesis Treatment Combined with Chemotherapy Produces Chondrosarcoma Necrosis," Clinical Cancer Research, vol. 9, 1211-1217, Mar. 2003.

Pharma Mar Press Release, "PharmaMar Differs with CPMP Opinion", Pharma Mar Grupo Zeltia, <<http://www.pharmamar.com/en/press/news_release.cfm>>, Jul. 24, 2003.

Pharma Mar Press Release, "PharmaMar Receives EMEA Appeal Decision on Yondelis in Soft Tissue Sarcoma", Pharma Mar Grupo Zeltia, <<http://www.pharmamar.com/en/press/news_release.cfm>>, Nov. 20, 2003.

Pharma Mar Press Release, "YONDELIS(r) STS-201 Efficacy and Safety Data Presented at ASCO 2007" Pharma Mar Grupo Zeltia, <<http://www.pharmamar.com/en/press>>, Jun. 5, 2007.

Pharma Mar Press Release, "The European Commission Authorizes YONDELIS(r) Commericalization for Soft Tissue Sarcoma" Pharma Mar Grupo Zeltia, <<http://www.pharmamar.com/en/press>>, Sep. 20, 2007.

Pommier et al., "DNA Sequence- and Structure-Selective Alkylation of Guanine N2 in the DNA Minor Groove by Ecteinascidin 743, a Potent Antitut:I1or Compound from the Caribbean Tunicate *Ecteinascidia turbinata*." Biochemistry 35, 13303-9, 1996.

Rinehart, K.L., "Antitumor Compounds from Tunicates." Med. Res. Rev. 20, 1-27, 2000.

Riccardi et al., "Preclinical Activity and Biodistribution of Ecteinascidin 743 (ET-743) and Doxorubicin (DOX) Combinations in Human Rhabdomyosarcoma," from the AACR-NCI-EORTC Conference on Molecular Targets and Cancer Therapeutics of Oct. 29-Nov. 2, 2001, Abstract 405.

Riccardi et al., "Effective Combinations of ET-743 and Doxorubicin for Tumor Growth Inhibitions Against Murine and Human Sarcomas in Athymic Mice," from the Proceedings of the AACR, vol. 42, Abstract 1132 (Mar. 2001).

Riccardi et al., "Combination of trabectedin and irinotecan is highly effective in a human rhabdomyosarcoma xenograft," Anti-Cancer Drugs, 16:811-815 (2005).

Riofrio, M. et al., "Ecteinascidin-743 (ET-743) 24 hours continuous infusion (CI): Clinical and pharmacokinetic phase I study progressive report," 23rd European Society for Medical Oncology Congress, Abstract 639P, Nov. 6-10, 1998.

Robert et al.,"Pharmacokinetics of Doxorubicin in Sarcoma Patients," Eur. J. Clin. Pharmocol., vol. 31, pp. 695-699, 1987.

Rosing et al., "Pharmacokinetics (PK) of Ecteinascidin-743 (ET-743) in three different phase I trials," Proceedings of the American Association for Cancer Research, vol. 40, pp. 81, abstract No. 542, Mar. 1999.

Ryan, D.P. "Studies with Ecteinascidin-743 (ET-743) A Marine Alkaloid," Cancer Invest, vol. 18 (suppl 1), pp. 112, abstract No. 87, Jan. 2000, from the Chemotherapy Foundation Symposium XVII Innovative Cancer Therapy for Tomorrow, Nov. 3-6, 1999, New York, NY.

Ryan, DP et al., "Phase I and Pharmacokinetic Study of Ecteinascidin-743 Administered as a 72 hours Continuous Intravenous Infusion in Patients with Solid Malignancies", Clinical Cancer Research, vol. 7, pp. 231-242, 2001.

Saito et al.,"Synthesis of Saframycins- 3," J. Org. Chem., 54, 5391, 1989.

Sakai et al., "Additional Antitumor Ecteinascidins from a Caribbean Tunicate: Crystal Structures and Activities in vivo," Proc. Natl. Acad. Sci., vol. 89, Dec. 1992, pp. 11456-11460.

Sato et al., "Multicenter Phase II Trial of Weekly Paclitazel for Advanced or Metastatic Breast Cancer: the Saitama Breast Cancer Clincal Study Group (SBCCSG-01)," Japanese Journal of Clinical Oncology, Vo. 33, No. 8, pp. 371-376, Aug. 2003.

Scotlandi et al., "Effectiveness of Ecteinascidin-743 against Drug-sensitive and—resistant Bone Tumor Cells," Clinical Cancer Research, 8:3893-3903 (Dec. 2002).

Scotto et al., "Ecteinascidin 743, a novel chemotherapeutic agent that targets transcriptional activation of a subset of genes, including MDR1," Clinical Cancer Research, vol. 6, Supplement, Abstract 210, p. 4508s, NCI-EORTC-AACR Symposium on New Drugs in Cancer Therapy, Nov. 7-10, 2000.

Sessa et al., "Trabectedin for Women with Ovarian Carcinoma After Treatment with Platinum and Taxane Fails," Journal of Clinical Oncology, vol. 23, No. 9, pp. 1867-1874, Mar. 20, 2005.

Shertzer et al., "Protection Against Carbon Tetrachloride Hepatoxicity by Pretreatment with indole-3-carbinol," Exptl. Molec. Pathol., vol. 46, pp. 180-189 (1987).

Shertzer et al., "Protection from N-Nitrosodimethylamine Mediated Liver Damage by Indole-3-carbinol," Exptl. Molec. Pathol., vol. 47, pp. 211-218 (1987).

Smyth, "Rationale for Drug Combinations," European Journal of Cancer, 39, 1816-1817 (2003).

Taamma, A. et al., "Ecteinascidin-743 (ET-743) 24 hours continuous infusion (CI): clinical and pharmacokinetic phase I study in solid tumor patients (PTS). Preliminary Results" 1998 ASCO Annual Meeting Proceedings, Abstract No. 890, 1998.

Taamma et al., "Ecteinascidin-743 (ET-743) 24 hour continuous intravenous infusion (CI) phase I study in solid tumors (ST) patients (pts)." Proceedings of the American Association for Cancer Research , vol. 39, pp. 323, abstract No. 2207, Mar. 1998.

Taamma, A. et al., "Phase I clinical study of ecteinascidin-743 (ET-743) as a 24 hours continuous intravenous infusion (CI) in patients (pts) with solid tumors (st): A progress report," ECCO, vol. 9, Abstract No. 1119, Sep. 18, 1997.

Taamma et al., "Phase I Clinical Study of ecteinascidin-743 (ET-743) as a 24 hours continuous intravenous infusion (CI) in patients (pts) with solid tumors (st): A progress report," Eur. J. Cancer, 33 Suppl. 8, S247-S248, Abstract, 1997.

Taamma et al., "Ecteinascidin-743 (ET-743) in heavily pretreated refractory sarcomas: early results of the French experience," Proceedings of the 1999 AACR-NCI-EORTC International Conference, Clinical Cancer Research, vol. 5, Supplement, p. 3791s, Abstract 309, Nov. 16-19, 1999.

Taamma et al., "Phase I and Pharmcokinetic Study of Ecteinascidin-743, a New Marine Compound, Adminstered as a 24 hours Continuous Infusion in Patients with Solid Tumors", J. of Clinical Oncology, vol. 19, No. 5, pp. 1256-1265, Mar. 1, 2001.

Tabor et al., "Anti oxidation Potential of Indole Compounds-Structure Activity Studies," Biological Reactive Intermediates IV, p. 833-836, 1990.

Takebayashi et al., "Poisoning of Human DNA Topoisomerase I by Ecteinascidin 743, An Anticancer Drug That Selectively Alkylates DNA in the Minor Groove." Proc. Natl. Acad. Sci. USA 96, 7196-201 1999.

Takebayashi et al., "Multidrug Resistance Induced by DNA Minor Groove Alkylation of Ecteinascidin 743 (Et743)," Proceedings of the 1999 AACR-NCI-EORTC International Conference, Clinical Cancer Research, vol. 5, Supplement, p. 3851s, Abstract 602, Nov. 16-19, 1999.

Takebayashi et al., "Nucleotide excision repair-dependent cytotoxicity of Ecteinascidin 743," Clinical Cancer Research, vol. 6, Supplement, Abstract 207, p. 4508s, NCI-EORTC-AACR Symposium on New Drugs in Cancer Therapy, Nov. 7-10, 2000.

Takahashi et al., "Ecteinascidin-743 (ET-743) and doxorubicin produce synergistic cytotoxic effects in soft tissue sarcoma lines HT-1080 and HS-18," Clinical Cancer Research, vol. 6, Abstract 208, Nov. 7-10, 2000.

Takahashi et al., "Sequence-dependent Enhancement of Cytotoxicity Produced by Ecteinascidin 743 (ET-743) with Doxorubicin or Paclitaxel in Soft Tissue Sarcoma Cells," Clinical Cancer Research, 7: 3251-3257 (Oct. 2001).

Takahashi et al., "Sequence-dependent Synergistic Cytotoxicity of Ecteinascidin-743 and Paclitaxel in Human Breast Cancer Cell Lines in Vitro and in Vivo," Cancer Research, 62: 6909-6915 (Dec. 1, 2002).

Ten Hagen et al., "Pegylated Liposomal Tumor Necrosis Factor—Alpha Results in Reduced Toxicity and Synergistic Antitumor Activity after Systemic Administration in Combination with Liposomal Doxorubicin (Doxil) in soft tissue Sarcoma-Bearing Rats," Int. J. Cancer, vol. 97, pp. 115-120, 2002.

Twelves, C.J. et al., "Phase I clinical and pharmacokinetic (PK) study of ecteinascidin-743 (ET-743) given as a one hour infusion every 21 days," 1998 ASCO Annual Meeting Proceedings, Abstract No. 889, 1998.

Twelves, C.J. et al., "Phase I and pharmacokinetic study of ecteinascidin-743 (ET-743) given as a one hour infusion every 21 days," ECCO, vol. 9, Abstract No. 1107, Sep. 18, 1997.

Twelves et al., "A Phase I and Pharmacokinetic (PK) study of Et-743 evaluating a 3 hours (h) intravenous (iv) infusion (I) in patients (pts) with solid tumors," Clinical Cancer Research, Abstract #307, 5 (11, suppl. 3790S-3791S), Nov. 16-19, 1999.

Twelves et al., "Phase I Trials with ET-743, a marine derived (MD) anticancer agent," Eur. J. Cancer, vol. 35, suppl. 4, p. S283, Abstract No. 1135, Sep. 15, 1999.

Valoti, G., et al., "Ecteinascidin-743 (ET-743), a marine natural compound, shows antitumor activity against human ovarian carcinoma xenografts," European Journal of Cancer (Novel Therapeutics and Pharmacology), vol. 34, Supp. 2, p. S39, Abstract PP179, 1998.

Valoti, G. "Ecteinascidin-743, a New Marine Natural Product with Potent Antitumor Activity on Human Ovarian Carcinoma Xenografts," Clin. Cancer Res., vol. 4, pp. 1977-1983, Aug. 1998.

van Kesteren et al., "Pharmacokinetics and Pharmacodynamics of the Novel Marine-derived Anticancer Agent Ecteinascidin 743 in a Phase I Dose-finding Study," Clinical Cancer Research, vol. 6, pp. 4725-2732, Dec. 2000.

van Kesteren et al. "Clinical Pharmacology of the Novel Marine-derived Anticancer Agent Ecteinascidin 743 Administered as a 1- and 3-h Infusion in a Phase I Study," Anti-Cancer Drugs, vol. 13, No. 4, pp. 381-393, Apr. 2002.

van Kesteren et al. "Yondelis® (trabectedin, ET-743): The Development of an Anticancer Agent of Marine Origin" Anti-Cancer Drugs, vol. 14, No. 7, pp. 487-502, Aug. 2003.

Villalona-Calero, M. et al., "A phase I and pharmacokinetic study of ET-743, a novel DNA minor groove binder of marine origin, administered as a 1-hour infusion daily +5 days," Annals Oncology, Abstract 453, 1998.

Villalona-Calero, M. et al., "Final results of a Phase I and pharmacokinetic (PK) study of the marine minor groove binder ET-743 on a daily + 5 schedule," 1999 ASCO Annual meeting proceedings, Abstract No. 691, May 15-18, 1999.

Weiwei et al., "Potent antitumor activity of ET-743 against human soft tissue sarcoma cell lines," Proceedings of the 1999 AACR-NCI-EORTC International Conference, Clinical Cancer Research, vol. 5, Supplement, p. 3790, Abstract 305, Nov. 16-19, 1999.

Wiesenthal, "Is one 'sensitive' drug better than another?" downloaded from internet website <<http://weisenthal.org/feedback.html>>, Feb. 4, 2002.

Wright et al., "Antitumor Tetrahydroisoquinonline Alkaloids from the Colonial Ascidian *Ecteinascidia turbinata*", J. Org. Chem., vol. 55, pp. 4508-4512, 1990.

Zelek et al., "Preliminary results of phase II study of ecteinascidin (ET-743) with the 24 hour (H) continuous infusion (CI) q3week Schedule in pretreated" Clinical Cancer Research, vol. 6, Supplement, Abstract 212, pp. 4508s-4509s, NCI-EORTC-AACR Symposium on New Drugs in Cancer Therapy, Nov. 7-10, 2000.

Zewail-Foote et al., "Ecteinascidin 743: A Minor Groove Alkylator that Bends DNA Toward the Major Groove," J. Med. Chem. 42, 2493-7, Jul. 15, 1999.

U.S. Appl. No. 09/546,877, filed Apr. 10, 2000, Rinehart.
U.S. Appl. No. 09/787,461, filed Mar. 2, 2001, Cvitkovich et al.
U.S. Appl. No. 10/416,086, filed Sep. 17, 2003, Naoto Takahashi.
U.S. Appl. No. 10/492,320, filed Oct. 21, 2002, Jimeno et al.
U.S. Appl. No. 10/524,152, filed Aug. 13, 2003, Esteban et al.
U.S. Appl. No. 10/540,092, filed Dec. 18, 2003, Iglesias et al.
U.S. Appl. No. 10/558,133, filed Nov. 15, 2006, D'Incalci et al.
U.S. Appl. No. 10/575,132, filed Oct. 14, 2004, Donald et al.
U.S. Appl. No. 10/579,130, filed May 12, 2006, Rowinsky et al.
U.S. Appl. No. 10/579,160, filed Mar. 1, 2007, Rybak.
U.S. Appl. No. 10/579,251, filed Oct. 20, 2006, Gianni et al.
U.S. Appl. No. 11/132,466, filed May 18, 2005, Rinehart et al.
U.S. Appl. No. 11/261,876, filed Oct. 28, 2005, Beijnen et al.
U.S. Appl. No. 11/571,589, filed Jan. 3, 2007, Rosell Costa.
U.S. Appl. No. 11/576,115, filed Sep. 28, 2005, Allavena et al.
U.S. Appl. No. 11/577,790, filed Apr. 23, 2007, Gilles et al.

Alexopoulos, "Phase II study of pegylated liposomal doxorubicin (Caelyx(R)) and docetaxel as first-line treatment in metastatic breast cancer," Ann. Oncol., 2004, 15(6):891-5.

Chabner, "Cytotoxic agents in the era of molecular targets and genomics," The Oncologist, vol. 7, suppl. 3, pp. 34-41, 2002.

Committee on Risk Assessment Methodology, "Issues in Risk Assessment. Appendix A: Workshop Summary- Maximum Tolerated Dose: Implications for Risk Assessment," National Research Council, National Academy of Sciences, National Academies Press, Washington DC, pp. 79-89, 1993.

D'Incalci et al., "Unique Features of the Mode of Action of ET-743", The Oncologist, 7, p. 210-216, Jun. 2002.

Donald et al, "Comparison of four modulators of drug metabolism as protectants against the hepatotoxicity of the novel antitumor drug yondelis (ET-743) in the female rat and in hepatocytes in vitro," Cancer Chemother Pharmacol, Apr. 2004, vol. 53, pp. 305-312.

European Medicines Agency (EMEA), "Scientific Discussion" from the European Public Assessment Report for Yondelis®, Revision 1, published Mar. 31, 2008, downloaded from the internet on Apr. 2, 2008, from the website <<http://www.emea.europa.eu/humandocs/Humans/EPAR/yondelis/yondelis.htm>>.

Forouzesh et al., Proc. Am. Soc. Clin. Oncol. ASCO meeting, Abstract 373, Jun. 3, 2001, Internet Archive Entry from the website <<http://web.archive.org/web/*/http://www.asco.org/>>, 32 pages.

Gourley C. et al., "Malignant mixed Mesodermal Tumours—Biology and Clinical Aspects," European Journal of Cancer, 2002, vol. 38, No. 11, pp. 1437-1446.

Halm et al., "A phase II study of pegylated liposomal doxorubicin for treatment of advanced hepatocellular carcinoma," Ann. Oncol., 2000, 11(1):113-114.

Hoekman at al., "A phase I/II study of dose-escalated docetaxel given two weekly in combination with a fixed dose of G-CSF," European Journal of Cancer, vol. 37, p. S76, Abstract 270, Oct. 22, 2001.

Horstmann et al., "Risks and Benefits of Phase I Oncology Trials, 1991 through 2002," New England Journal of Medicine, vol. 352, pp. 895-904; Mar. 3, 2005.

Hussein et al., "A Phase II Trial of Pegylated Liposomal Doxorubicin, Vincristine, and Reduced-Dose Dexamethasone Combination Therapy in Newly Diagnosed Multiple Myeloma Patients," Cancer, Nov. 15, 2002, vol. 95, No. 10, pp. 2160-2168.

Lau et al., "A Phase I and Pharmacokinetic Study of Ecteinascidin-743 (Yondelis) in Children with Refractory Solid Tumors." Clinical Cancer Research, vol. 11, pp. 672-677, Jan. 15, 2005.

PR Newswire, Oct. 14, 2001, 4 pages.

Puchalski et al., "Pharmacokinetics of Ecteinascidin 743 Administered as a 24-h Continuous Intravenous Infusion to Adult Patients with Soft Tissue Sarcomas associations with Clinical Characteristics, Pathophysiological Variables and Toxicity," Cancer Chemotherapy and Pharmacology, 2002, vol. 50, No. 4, pp. 309-319.

Rote Liste 2002 "Doxorubicin," entries 86-056 through 86-062, 2002.

Sarosy et al., "Phase I Study of α2-interferon plus Doxorubicin in Patients with Solid Tumors," Cancer Research, vol. 46, pp. 5368-5371, 1986.

Schwartsmann G. et al., "Marine Organisms as a Source of New Anticancer Agents," The Lancet Oncology, 2001, vol. 2, No. 4, pp. 221-225.

Twelves et al., "Phase I and pharmacokinetic study of YondelisTM (Ecteinascidin-743; ET-743) administered as an infusion over 1 h or 3 h every 21 days in patients with solid tumours," European Journal of Cancer, vol. 39, p. 1842-1851, 2003; available online Aug. 14, 2003.

Wollina, "Multicenter study of pegylated liposomal doxorubicin in patients with cutaneous T-cell lymphoma," Cancer 2003, 1:98(5):993-1001, published online Jul. 24, 2003.

Brien et al., "Reduced Cardiotoxicity and Comparable Efficacy in a Phase III Trial of Pegylated Liposomal Doxorubicin HCl (CAELYX™/Doxil®) Versus Conventional Doxorubicin for First-Line Treatment of Metastatic Breast Cancer," Annals of Oncology, vol. 15, pp. 440-449, 2004.

Chinese J. New Drugs Clin. Rem., 2001, pp. 216, 219.

Cvetkovic et al., "ET-743," Drugs, vol. 62(8), pp. 1185-1192, 2002.

Gogas et al., "Neoadjuvant Chemotherapy with a Combination of Pegylated Liposomal Doxorubicin (Caelyx®) and Paclitaxel in Locally Advanced Breast Cancer: A Phase II Study by the Hellenic Cooperative Oncology Group," Annals of Oncology, pp. 1737-1742, 2002.

Hosomi et al., "Phase I Study of Cisplatin and Docetaxel Plus Mitomycin C in Patients with Metastatic Non-Small Cell Lung Cancer," Jpn. J. Clin. Oncol., 29(11), pp. 546-549, 1999.

McMeekin et al., "Trabectedin (T) in Relapsed Advanced Ovarian Cancer (ROC): A Pooled Analysis of Three Phase II Studies," Journal of Clinical Oncology, 25(18S), Abstract No. 5579, 2007 ASCO Annual Meeting.

Pasetto et al., "Improved Tolerability of Chemotherapy in Soft Tissue Sarcomas: Old and New Strategies," Expt. Rev. Antican. Ther., vol. 3(2), pp. 167-178, 2003.

Villalona-Calero et al., "A Phase I and Pharmacokinetic Study of Ecteinascidin-743 on a Daily × 5 Schedule in Patients with Solid Malignancies," Clinical Cancer Research, vol. 8, pp. 75-85, 2002.

Zeltia Group Annual Report 2002.

Zeltia, Junta General de Accionistas 2003.

Aboussekhra, A. et al. "Mammalian DNA Nucleotide Excision Repair Reconstituted with Purified Protein Components" Cell 1995, 80, 859-868.

Andya et al., "Mechanisms of Aggregate Formation and Carbohydrate Excipient Stabilization of Lyophilized Humanized Monoclonal Antibdoy Formulations," AAPS PharmSci, 5(2), pp. 1-11, 2003.

Bootsma, D. et al. The Genetic Basis of Human Cancer, $1^{st}$ ed.; Vogelstein B, Kinzler KW Eds.; McGraw Hill: Toronto, 1998; pp. 245-274.

Bueren, J. A. et al. Generation of DNA double strand breaks Turing trabectedin DNA damage measured trough induction of γH2AX [abstract]. In: American Association for Cancer Research Annual Meeting; Proceedings; Apr. 14-18, 2007; Los Angeles, CA. Philadelphia (PA): AACR; 2007. Abstract nr 1965; and the corresponding poster presented in said congress.

Casali et al., "Activity of Ecteinascidin-743 (ET-trabectedin) 3-hour Infusion in Adult and Childhood Small Round Cell Sarcomas," ASCO Annual Meeting, 2003, Abstract 962.

Damia, G. et al. ET743-Induced changes in gene expression in murine cells defective in nucleotide excision repair [abstract]. In: AACR-NCI-EORTC International Conference on Molecular Targets and Cancer Therapeutics; Oct. 22-Nov. 2, 2001; Miami, US. Philadelphia (PA): ACCR, 2001. Abstract No. 666.

Erba, E. et al. "Ecteinascidin-743 (ET-743), a natural marine compound, with a unique mechanism of action" Eur. J. Cancer 2001, 37, 97-105.

Garcia-Carbonero et al., "Ecteinascidin-743 (ET-743) for Chemotherapy-Naïve Patients with Advanced Soft Tissue Sarcomas: Multicenter Phase II and Pharmacokinetic Study," J. Clin. Oncol. 23:5484-5492, 2005.

Grazziotin Soares, D. et al. "Low cytotoxicity of ecteinascidin 743 in yeast lacking the major endonucleolytic enzymes of base and nucleotide excision repair pathways" Biochemical Pharmacology 2005, 70, 59-69.

Grazziotin Soares, D. et al. "Replication and homologous recombination repair regulate DNA double-strand break formation by the antitumor alkylator ecteinascidin 743" PNAS 2007, 104, 13062-13067.

Grosso, F. et al. Trabectedin (T) in soft tissue sarcomas (STS) carrying a chromosomal translocation: an exploratory analysis [abstract]. In: $13^{th}$ CTOS Annual Meeting; Nov. 1-3, 2007; Seattle, WA. p. 51. Abstract nr 900; and the corresponding oral presentation presented en said congress.

Herrero, A. B. et al. "Cross-Talk between Nucleotide Excision and Homologous Recombination DNA Repair Pathways in the Mechanism of Action of Antitumor Trabectedin" Cancer Res. 2006, 66, 8155-8162.

Ilson et al., "A Phase II Trial of Paclitaxel and Cisplatin in Patients with Advanced Carcinoma of the Esophagu," Cancer J, 6(5), 316-23, 2000.

Italiano, A. et al. ERCC5 (XPG) status and clinical activity of trabectedin in patients with advanced soft-tissue sarcoma [abstract]. In: Proceedings of the $101^{th}$ Annual Meeting of the American Association for Cancer Research; Apr. 17-21, 2010; Washington, DC. Philadelphia (PA): AACR; 2010. Abstract No. 2699; and the corresponding poster presented in said congress.

Kesteren Ch. Van et al. "Yondelis® (trabectedin, ET-743): the development of an anticancer agent of marine origin" Anti-Cancer Drugs 2003, 14, 487-502.

Kononen, J. et al. "Tissue microarrays for high-throughput molecular profiling of tumor specimens" Nature Med. 1998, 4, 844-847.

Kraemer, K. H. et al. "The Role of Sunlight and DNA Repair in Melanoma and Nonmelanoma Skin Cancer. The Xeroderma Pigmentosum Paradigm" Arch. Dermatol. 1994, 130, 1018-1021.

Kraemer, K. H. et al. "Xeroderma Pigmentosum. Cutaneous, Ocular, and Neurologic Abnormalities in 830 Published Cases" Arch. Dermatol. 1987, 123, 241-250.

Krafft, A. E. et al. "Optimization of the Isolation and Amplification of RNA From Formalin-fixed, Paraffin-embedded Tissue: The Armed Forces Institute of Pathology Experience and Literature Review" Mol. Diagn. 1997, 2, 217-230.

Lau et al., "A Phase I and Pharmacokinetic Study of Ecteinascidin-743 (Yondelis) in Children with Refractory Solid Tumors." Clinical Cancer Research, vol. 11, pp. 672-677, Jan. 15, 2005.

Le Morvan, V. et al. Genetic polymorphisms of the XPG and XPD nucleotide excision repair genes in sarcoma patients [abstract]. In: Proceedings of the $96^{th}$ Annual Meeting of the American Association for Cancer Research; Apr. 16-20, 2005; Anaheim/Orange County, CA. Philadelphia (PA): AACR; 2005. Abstract No. 4099.

Le Morvan, V. et al. "Genetic polymorphisms of the XPG and XPD nucleotide excision repair genes in sarcoma patients" Int. J. Cancer 2006, 119, 1732-1735.

Le Page, F. et al. "Transcription-Coupled Repair of 8-oxoGuanine: Requirement for XPG, TFIIH, and CSB and Implications for Cockayne Syndrome" Cell 2000, 101, 159-171.

Martinez, N. et al. "Transcriptional signature of Ecteinascidin 743 (Yondelis, Trabectedin) in human sarcoma cells explantes from chemo-naïve patients" Mol. Cancer Ther. 2005, 4, 814-823.

Moneo, V. et al. "Extreme Sensitivity to Yondelis® (Trabectedin, ET-743) in Low Passaged Sarcoma Cell Lines Correlates With Mutated p53" J. Cell. Biochem. 2007, 100, 339-348.

Monk et al., "A Randomized Phase III Study of Trabectedin With Pegylated Liposmal Doxorubicin (PLD) Versus PLD in Relapsed, Recurrent Ovarian Cancer (OC)," Annals of Oncology, 19(8), 2008.

Mu, D. et al. "Reaction Mechanism of Human DNA Repair Excision Nuclease" J. Biol. Chem. 1996, 271, 8285-8294.

Mudgett. J. S. et al. "Isolation of the Functional Human Excision Repair Gene ERCC5 by Intercosomid Recombination" Genomics 1990, 8, 623-633.

Nouspikel, T. et al. "Mutations that disable the DNA repair gene XPG in a xeroderma pigmentosum group G patient" Hum. Mol. Genet. 1994, 3, 963-967.

O'Donovan, A. et al. "Identical defects in DNA repair in xeroderma pigmentosum group G and rodent ERCC group 5" Nature 1993, 363, 185-188.

Pourquier, P. et al. Nucleotide excision repair-mediated cytotoxicity of ecteinascidin 743, a novel anticancer agent in clinical trials [abstract]. In: Proceedings of the $92^{nd}$ Annual Meeting of American Association for Cancer Research; Mar. 24-28, 2001; New Orleans, LA, USA. Philadelphia (PA): AACR; 2001. p. 556. Abstract No. 2987.

Rimassa et al., "Unexpected Low Efficacy of Stealth Liposomal Doxorubicin (Caelyx) and Vinorelbine in Metastatic Breast Cancer," Breast Cancer Research and Treatment, 77, 2003, pp. 185-188.

Rose et al., "A Phase I Trial of Prolonged Oral Etoposide and Liposomal Doxorubicin in Ovarian, Peritoneal, and Tubal Carcinoma: A Gynecologic Oncology Group Study," Gynecologic Oncology, 85, 2002, pp. 136-139.

Rosell, R. et al. Expression of XPG mRNA and protein as potential biomarker of response to trabectedin in sarcoma patients [abstract]. In: AACR-NCI-EORTC International Conference on Molecular Targets and Cancer Therapeutics; Oct. 22-26, 2007; San Francisco, CA. Philadelphia (PA): AACR; 2007. Abstract No. C127; and the corresponding poster presented in said congress.

Rosell, R. et al. DNA repair efficiency as a model for personalizaed therapy with Trabectedin [abstract]. In: AACR Molecular Diagnostic in Cancer Therapeutic Development; Sep. 17-20, 2007; Atlanta, GA. Philadelphia (PA): AACR; 2007. p. 44. Abstract nr A57; and the corresponding poster presented in said congress.

Schöffski. P. et al. DNA repair functionality as a molecular signature for sensitivity(S)/resistance(R) in sarcoma patients (pts) treated with trabectedin (ET-743, Yondelis®) [abstract]. In: American Association for Cancer Research Annual Meeting: Proceedings; Apr. 14-18, 2007; Los Angeles, CA. Philadelphia (PA): AACR; 2007. Abstract nr 144; and the corresponding poster presented in said congress.

Scotto, Anticancer Drugs, May 2002, 13 Suppl 1, S3-6.

Shimizu et al., "Phase I Study of Docetaxel and Cyclophosphamide in Patients with Advanced or Recurrent Breast Cancer," Breast Cancer, 10(2), pp. 140-148, Apr. 2003.

Sparano et al., "Phase I Trial of Pegylated Liposomal Doxorubicin and Docetaxel in Advanced Breast Cancer," J. Clinical Oncology, vol. 19(12), pp. 3117-3125, 2001.

Specht, K. et al. "Quantitative Gene Expression Analysis in Microdissected Archival Formalin-Fixed and Paraffin-Embedded Tumor Tissue" Am. J. Pathol. 2001, 158, 419-429.

Stevens, E. et al. Ecteinascidin-743 (Et-743) and Transcription-Coupled Nucleotide Excision Repair (TC-NER): Translational and Clinical Study in Ovarian Cancer [abstract]. In: Proceedings of the $94^{th}$ Annual Meeting of the American Association for Cancer Research; Jul. 11-14, 2003; Washington, DC, Philadelphia (PA): AACR; 2003. Abstract No. 468.

Stevens, E. V. et al. "Prediciting cisplatin and trabectedin drug sensitivity in ovarian and colon cancers" Mol. Cancer Ther. 2008, 7, 10-18.

Takebayashi, Y. et al. "Antiproliferative activity of ecteinascidin 743 is dependent upon transcription-coupled nucleotide-excision repair" Nature Med. 2001, 7, 961-966.

Takebayashi, Y. "Loss of heterozygosity of nucleotide excision repair factors in sporadic ovarian, colon and lung carcinomas: implications for their roles of carcinogenesis in human solid tumors" Cancer Lett. 2001, 174, 115-125.

Taron, M. et al, BRCA1 expression and customized chemotherapy [abstract]. In: Eurocancer. XX Congress; Jun. 26-28, 2007; Paris. Paris: John Libbey Eurotext, 2007. pp. 107-108.

Tercero, J. C. et al, Predicting sarcoma patients response to trabectedin treatment with molecular markers detected by inmunohistochemistry [abstract] In: AACR International Conference: Molecular Diagnostics in Cancer Therapeutic Development; Sep. 22-25, 2008; Philadelphia, PA. Philadelphia (PA): AACR, 2008. p. 44. Abstract nr B8; and the corresponding poster presented in said congress.

van Steeg, H et al., "Xeroderma pigmentosum and the role of UV-induced DNA damage in skin cancer" Mol. Med. Tod. 1999, 5, 86.

Wakasugi, M. et al., "The Non-catalitc Function of XPG Protein during Dual Incision Human Nucleotide Excision Repair," J. Biol. Chem., 1997, 272, 16030-16034.

Yondelis Summary of Product Characteristics as authorised by EMA in 2007.

Zewail-Foote, M. et al., "The inefficiency of incisions of ecteinascidin 743-DNA adducts by the UvrABC nuclease and the unique structural feature of the DNA adducts can be used to explain the repair-dependent toxicities of the antitumor agent," Chemistry & Biology, 2001, 8, 1033-1049.

Notice of Opposition filed against European Patent No. 1827500 by Teva Pharmaceuticals Industries Ltd. dated Feb. 5, 2010.

Response to Notice of Opposition against European Patent No. 1827500 dated Feb. 10, 2011.

Therasse et al., J. National Cancer Inst., 92(3):205-16, 2000.

Green et al., Investigational New Drugs, 10:239-253, 1992.

Miller et al., Cancer, 47:207-214, 1981.

Rustin et al., Clinical Cnacer Research, 10:3919-3926, 2004.

U.S. Appl. No. 10/257,856, filed Mar. 31, 2003, Andres Francesch.

U.S. Appl. No. 12/094,744, filed Nov. 17, 2008, Kathleen Scotto.

U.S. Appl. No. 12/299,960, filed Mar. 23, 2009, Yusri Ali Elsayed.

U.S. Appl. No. 12/552,347, filed Sep. 2, 2009, Naoto Takahashi.

\* cited by examiner

Figure 1

| Sched. | Pts | Dose | RD* | Cycles | Tumor Type | Previous Chem. Lines | Response | Time to progression (months) |
|---|---|---|---|---|---|---|---|---|
| 1h | 40 | 585 | 1000 | 10 | Melanoma |  | pCR | 29+ |
| 3h | 32 | 1500 | 1500 | 10 | Leiomyosarcoma | 1 | CR | 12 |
|  |  | 1650 |  | 13+ | Colon Stromal Sarcoma | 1 | PR | 10+ |
|  |  | 1650 |  | 5+ | Gastric Stromal Sarcoma | 1 | MR | 4+ |
| 24h | 52 | 1500 | 1500 | 5 | Osteosarcoma | 4 | PR | 2 |
|  |  | 1500 |  | 12 | Liposarcoma | 2 | PR | 15+ |
|  |  | 1800 |  | 3 | Breast | 2 | PR | 3 |
| dx5 | 42 | 325x5 | 1625 | 6 | Leiomyosarcoma | 1 | MR (27%) | 4 |
|  |  | 325x5 |  | 7 | Ovarian | 7 | MR+fall CA 125 | 6 |
| 72h | 21 | 1200 | 1050 | 6 | Mesothelioma | 1 | MR (41%) | 5 |
|  |  | 1200 |  | 4 | Ocular Melanoma |  | Mixed R | 2 |

Total Pts 187

COMPOSITIONS AND USES OF ET743 FOR TREATING CANCER

This application claims priority under 35 U.S.C. §120 to U.S. Ser. No. 09/787,461, filed Mar. 2, 2001 (abandoned), which is the national phase entry of PCT/GB00/01857, filed May 15, 2000, which claims the benefit of GB 9911183.3, filed May 13, 1999, GB9911346.6, filed May 14, 1999, GB 9918534.0, filed Aug. 5, 1999, GB 9927005.0, filed Nov. 15, 1999, GB 9927106.6, filed Nov. 16, 1999, and GB 0007637.2, filed Mar. 29, 2000, the disclosures of which are incorporated by reference.

FIELD OF INVENTION

The present invention relates to the treatment of cancers with Et 743.

BACKGROUND OF INVENTION

Cancer comprises a group of malignant neoplasms that can be divided into two categories, carcinoma, comprising a majority of the cases observed in the clinics, and other less frequent cancers, which include leukemia, lymphoma, central nervous system tumours and sarcoma. Carcinomas have their origin in epithelial tissues while sarcomas develop from connective tissues and those structures that had their origin in mesoderm tissues. Sarcomas can affect, for instance, muscle or bone and occur in the bones, bladder, kidneys, liver, lung, parotid or spleen.

Cancer is invasive and tends to metastasise to new sites. It spreads directly into surrounding tissues and also may be disseminated through the lymphatic and circulatory systems. Many treatments are available for cancer, including surgery and radiation for localised disease, and drugs. However, the efficacy of available treatments on many cancer types is limited, and new, improved forms of treatment showing clinical benefit are needed.

This is especially true for those patients presenting with advanced and/or metastatic disease. It is also true for patients relapsing with progressive disease after having been previously treated with established therapies for which further treatment with the same therapy is mostly ineffective due to acquisition of resistance or to limitations in administration of the therapies due to associated toxicities.

Chemotherapy plays a significant part in cancer treatment, as it is required for treatment of advanced cancers with distant metastasis and often helpful for tumor reduction before surgery, and many anti-cancer drugs have been developed based on various modes of action.

The ecteinascidins are marine alkaloids and some of them possess potent in vitro antitumour activity. Several ecteinascidins have been reported previously in the patent and scientific literature.

For example, U.S. Pat. No. 5,089,273 describes novel compositions of matter extracted from the tropical marine invertebrate, *Ecteinascidia turbinata*, and designated therein as ecteinascidins 729, 743, 745, 759A, 759B and 770. These compounds are useful as antibacterial and/or antitumour agents in mammals.

U.S. Pat. No. 5,256,663 describes pharmaceutical compositions comprising matter extracted from the tropical marine invertebrate, *Ecteinascidia turbinata*, and designated therein as ecteinascidins, and the use of such compositions as antibacterial, anti-viral, and/or antitumour agents in mammals.

U.S. Pat. No. 5,478,932 describes ecteinascidins isolated from the Caribbean tunicate *Ecteinascidia turbinata*, which provide in vivo protection against P388 lymphoma, B16 melanoma, M5076 ovarian sarcoma, Lewis lung carcinoma, and the LX-1 human lung and MX-1 human mammary carcinoma xenografts.

U.S. Pat. No. 5,654,426 describes several ecteinascidins isolated from the Caribbean tunicate *Ecteinascidia turbinata*, which provide in vivo protection against P388 lymphoma, B16 melanoma, M5076 ovarian sarcoma, Lewis lung carcinoma, and the LX-1 human lung and MX-1 human mammary carcinoma xenografts.

U.S. Pat. No. 5,721,362 describes a synthetic process for the formation of ecteinascidin compounds and related structures.

Further background is to be found illustratively in: Corey, E. J., J. Am. Chem. Soc., 1996, 118 pp. 9202-9203; Rinehart, et al., Journal of National Products, 1990, "Bioactive Compounds from Aquatic and Terrestrial Sources", vol. 53, pp. 771-792; Rinehart et al., Pure and Appl. Chem., 1990, "Biologically active natural products", vol. 62, pp. 1277-1280; Rinehart, et al., J. Org. Chem., 1990, "Ecteinascidins 729, 743, 745, 759A, 759B, and 770: Potent Antitumour Agents from the Caribbean Tunicate *Ecteinascidia turbinata*", vol. 55, pp. 4512-4515; Wright et al., J. Org. Chem., 1990, "Antitumour Tetrahydroisoquinoline Alkaloids from the Colonial Ascidian *Ecteinascidia turbinata*", vol. 55, pp. 4508-4512; Sakai et al., Proc. Natl. Acad. Sci. USA 1992, "Additional antitumour ecteinascidins from a Caribbean tunicate: Crystal structures and activities in vivo", vol. 89, 11456-11460; Science 1994, "Chemical Prospectors Scour the Seas for Promising Drugs", vol. 266, pp. 1324; Koenig, K. E., "Asymmetric Synthesis", ed. Morrison, Academic Press, Inc., Orlando, Fla., vol. 5, 1985, p. 71; Barton, et al., J. Chem. Soc. Perkin Trans., 1, 1982, "Synthesis and Properties of a Series of Sterically Hindered Guanidine Bases", pp. 2085; Fukuyama et al., J. Am. Chem. Soc., 1982, "Stereocontrolled Total Synthesis of (+)-Saframycin B", vol. 104, pp. 4957; Fukuyama et al., J. Am. Chem. Soc., 1990, "Total Synthesis of (+)-Saframycin A", vol. 112, p. 3712; Saito, et al., J. Org. Chem., 1989, "Synthesis of Saframycins. Preparation of a Key Tricyclic Lactam Intermediate to Saframycin A", vol. 54, 5391; Still, et al., J. Org. Chem., 1978, "Rapid Chromatographic Technique for Preparative Separations with Moderate Resolution", vol. 43, p. 2923; Kofron, W. G.; Baclawski, L. M., J. Org. Chem., 1976, vol. 41,1879; Guan et al., J. Biomolec. Struc. & Dynam., vol. 10 pp. 793-817 (1993); Shamma et al., "Carbon-13 NMR Shift Assignments of Amines and Alkaloids", p. 206 (1979); Lown et al., Biochemistry, 21, 419-428 (1982); Zmijewski et al., Chem. Biol. Interactions, 52, 361-375 (1985); Ito, CRC CRIT. Rev. Anal. Chem., 17, 65-143 (1986); Rinehart et al., "Topics in Pharmaceutical Sciences 1989" pp. 613-626, D. D. Breimer, D. J. A. Cromwelin, K. K. Midha, Eds., Amsterdam Medical Press B. V., Noordwijk, The Netherlands (1989); Rinehart et al., "Biological Mass Spectrometry", 233-258 eds. Burlingame et al., Elsevier Amsterdam (1990); Guan et al., Jour. Biomolec. Struct. & Dynam., vol. 10 pp. 793-817 (1993); Nakagawa et al., J. Amer. Chem. Soc., 111: 2721-2722 (1989); Lichter et al., "Food and Drugs from the Sea Proceedings" (1972), Marine Technology Society, Washington, D.C. 1973, 117-127; Sakai et al., J. Amer. Chem. Soc. 1996, 118, 9017; Garcia-Rocha et al., Brit. J. Cancer, 1996, 73: 875-883; and Pommier et al., Biochemistry, 1996, 35: 13303-13309.

In particular, ecteinascidin 743 has been found also to exhibit promising action when tested in animal models, as, for example, when evaluated against xenografts of breast cancer, non-small cell lung, melanoma and ovarian cancer.

A paper on in vitro antitumour activity of the novel marine agent, Ecteinascidin-743 (ET-743, NSC-648766) against human tumours explanted from patients, Annals of Oncology, 9: 981-987, 1998, is typical of the in vivo reports. The authors conclude from their data that continuous or protracted exposure may enhance activity. In the same issue of that journal at pages 989-993, a paper on in vitro schedule-dependency of myelotoxicity and cytotoxicity of Ecteinascidin 743 (ET-743) concludes that prolonged exposure might represent the best schedule of administration.

SUMMARY OF INVENTION

We have developed a method to treat human patients with ET743 leading to clinical improvement.

BRIEF DESCRIPTION OF THE DRAWINGS

FIG. 1 shows responses observed with this method of treatment.

EMBODIMENTS OF THE INVENTION

Thus, the present invention provides a method of treating any mammal notably a human, affected by cancer which comprises administering to the affected individual a therapeutically effective amount of ET743, or a pharmaceutical composition thereof.

The present invention also relates to pharmaceutical preparations, which contain as active ingredient ET743, as well as the processes for their preparation.

Examples of pharmaceutical compositions include liquid (solutions, suspensions or emulsions) with suitable composition for intravenous administration, and they may contain the pure compound or in combination with any carrier or other pharmacologically active compounds.

Administration of the compounds or compositions of the present invention is by intravenous infusion. We prefer that infusion times of up to 72 hours are used, more preferably 2 to 24 hours, with either about 3 or about 24 hours most preferred. Short infusion times which allow treatment to be carried out without an overnight stay in hospital are especially desirable. However, infusion may be around 24 hours or even longer if required. Infusion may be carried out at suitable intervals of say 1 to 6 weeks. Further guidance is given later in this text.

The correct dosage of the compound will vary according to the particular formulation, the mode of application, and the particular situs host and tumour being treated. Other factors like age, body weight, sex, diet, time of administration, rate of excretion, condition of the host, drug combinations, reaction sensitivities and severity of the disease shall be taken into account. Administration can be carried out continuously or periodically within the maximum tolerated dose.

The compound ET743 and compositions of this invention may be used with other drugs to provide a combination therapy. The other drugs may form part of the same composition, or be provided as a separate composition for administration at the same time or a different time. The identity of the other drug is not particularly limited, and suitable candidates include:

- a) drugs with antimitotic effects, especially those which target cytoskeletal elements, including microtubule modulators such as taxane drugs (such as taxol, paclitaxel, taxotere, docetaxel), podophylotoxins or vinca alkaloids (vincristine, vinblastine);
- b) antimetabolite drugs (such as 5-fluorouracil, cytarabine, gemcitabine, purine analogues such as pentostatin, methotrexate);
- c) alkylating agents or nitrogen mustards (such as nitrosoureas, cyclophosphamide or ifosphamide);
- d) drugs which target DNA such as the antracycline drugs adriamycin, doxorubicin, pharmorubicin or epirubicin;
- e) drugs which target topoisomerases such as etoposide;
- f) hormones and hormone agonists or antagonists such as estrogens, antiestrogens (tamoxifen and related compounds) and androgens, flutamide, leuprorelin, goserelin, cyprotrone or octreotide;
- g) drugs which target signal transduction in tumour cells including antibody derivatives such as herceptin;
- h) alkylating drugs such as platinum drugs (cis-platin, carbonplatin, oxaliplatin, paraplatin) or nitrosoureas;
- i) drugs potentially affecting metastasis of tumours such as matrix metalloproteinase inhibitors;
- j) gene therapy and antisense agents;
- k) antibody therapeutics;
- l) other bioactive compounds of marine origin, notably the didemnins such as aplidine;
- m) steroid analogues, in particular dexamethasone;
- n) anti-inflammatory drugs, including nonsteroidal agents (such as acetaminophen or ibuprofen) or steroids and their derivatives in particular dexamethasone; and
- o) anti-emetic drugs, including 5HT-3 inhibitors (such as gramisetron or ondasetron), and steroids and their derivatives in particular dexamethasone.

The present invention also extends to the compounds of the invention for use in a method of treatment, and to the use of the compounds in the preparation of a composition for treatment of cancer.

Patient responses have been observed in clinical trials with ET-743, demonstrating usefulness of the method of treatment.

Phase I clinical studies and pharmacokinetic analysis demonstrate that ET-743 presents a positive therapeutic window with manageable toxicity in the range of dosage required for clinical efficacy in the treatment of cancer patients.

The method consists of administration of drug by intravenous infusion over a period of 72 hrs or less at the recommended dose level (RD) with or without combination with other therapeutic agents.

ET-743 is supplied and stored as a sterile lyophilized product, consisting of ET 743 and excipient in a formulation adequate for therapeutic use, in particular a formulation containing mannitol and a phosphate salt buffered to an adequate pH.

A preferred formulation, which shows improved stability at higher storage temperature, is one obtained from 1000 ml of 0.9% sodium chloride or other suitable infusion vehicle, 250 μg of ET-743 with 250 mg of mannitol, 34 mg of monopotassium phosphate and phosphoric acid to adjust to a pH between 4.00 and 6.00, with 4.80 being the preferred pH. The product is lyophilized and stored in the cold, between +4° C. and −20° C. and protected from light until use.

Preparation of the reconstituted solution is performed under aseptic conditions by adding distilled water in the amount of 5 ml for every 250 μg of ET-743 and shaking for a short time to dissolve the solids.

Preparation of the infusion solution is also performed under aseptic conditions by withdrawing the reconstituted solution volume corresponding to dosage calculated for each patient, and slowly injecting the required reconstituted solution volume into an infusion bag or bottle containing between 100 and 1000 ml of 0.9% sodium chloride solution, after which the whole is homogenised by slow manual shaking. The ET-743 infusion solution should be administered intravenously, as soon as possible, within 48 hours after preparation. PVC and polyethylene infusion systems, as well as clear glass are preferred container and conduit materials.

The administration is performed in cycles, in the preferred application method, an intravenous infusion of ET734 is given to the patients the first week of each cycle, the patients are allowed to recover for the remainder of the cycle. The preferred duration of each cycle is of either 3 or 4 weeks; multiple cycles can be given as needed. The drug may also be administered each of the first days of each cycle. Dose delays and/or dose reductions and schedule adjustments are performed as needed depending on individual patient tolerance of treatments, in particular does reductions are recommended for patients with higher than normal serum levels of liver transaminases or alkaline phosphatase, or bilirubin.

The Recommended Dose (RD) is the highest dose which can be safely administered to a patient producing tolerable, manageable and reversible toxicity according to the Common Toxicity Criteria established by the National Cancer Institute (USA), with no more than 2 out of 6 patients presenting any dose limiting toxicities (DLT). Guidelines for cancer therapy frequently call for administration of chemotherapeutic agents at the highest safe dose at which toxicity is manageable in order to achieve maximum efficacy (DeVita, V. T. Jr., Hellman, S, and Rosenberg, S. A., Cancer: Principles and Practice of Oncology, 3rd ed., 1989, Lipincott, Philadelphia).

DLTs for ET743 using this method of treatment were determined in clinical studies to be myelosuppression and malaise. These studies established a recommended dose level of 1500 microgram per m2 of body surface area for 24 hr infusions or 1650 microgram per m2 body surface area for 3 hr infusions. Doses of 1800 microgram per m2 or above resulted in too large a fraction of patients presenting DLT and thus were determined to be too toxic for safe administration.

Whereas a case of a breast cancer response reported in June 98 was observed at a dose level of 1800 microgram m2, a level considered unsafe at any rate on infusion because 2 out of 4 patients presented severe dose limiting toxic responses. Another previously reported case involved a response in a melanoma patient after a 1 hr infusion, which method does not allow reaching the recommended dose level without dose limiting thrombocytopenia and fatigue.

ET-743 can be safely administered at a dosage level at or below the Recommended Dose (RD).

In particular intravenous infusion over 24 hr at a dose level between 500 and 1500 microgram per m2 of body surface area, preferably, between 1000 and 1500 microgram per m2 of body surface area, the latter being the RD for this schedule as determined in clinical trials ea.

In particular intravenous infusion is suitably performed over 3 hr at a dose level between 500 and 1650 microgram per m2 of body surface area, preferably, between 1000 and 1650 microgram per m2 of body surface area, the latter being the RD for this schedule as determined in clinical trials. Other forms of treatment include intravenous infusion over 72 hr at the RD for this schedule of 1050 microgram per m2 of body surface area.

An alternative procedure is an intravenous infusion over 5 consecutive days, 24 hr daily, at the RD for this schedule of 1625 microgram per m2 of body surface area.

When ET 743 is used in combination with other therapeutic agents, the dosages of both agents may need to be adjusted.

Previously the only biological responses reported to the administration of ET743 had been observed in animal or in vitro models, known to be notoriously inaccurate concerning their usefulness to predict responses in human patients, or in human patients in experimental settings where an effective, safe method of treatment was unavailable (either the dosage used was a toxic dose significantly elevated over the recommended dose or the administration schedule was not appropriate).

In clinical trials using the method of this invention, appropriate plasma levels were achieved in patients at RD, and most importantly, objectively measurable responses demonstrated evidence of clinical benefit to patients.

Definitions for patient responses are adopted from WHO Common Toxicity Criteria and the responses determined following standard medical practice in the field.

Objective responses were obtained in patients with advanced and/or metastatic cancers refractory to previous treatments, which included soft tissue, bone and gastrointestinal stromal sarcoma, breast cancer and melanoma. Evidence of activity, using a variety of suboptimal schedules which has also been observed in advanced ocular melanoma and mesothelioma, and a positive clinical marker response in ovarian cancer suggests the method of this invention will be useful in the treatment of these diseases as well.

In particular treatment with this method has shown responses in cancer patients with advanced and/or metastatic disease, which exhibited progressive disease after having been previously treated with established therapies.

A preferred method of this invention therefore involves identifying cancer patients who have been treated for cancer, particularly patients who have received chemotherapy, and treating them with ET743.

In particular treatment with this method has also shown responses in patients with sarcomas including soft tissue, bone and gastrointestinal stromal sarcomas. In particular treatment with this method has shown responses in patients with soft tissue sarcomas. In particular treatment with this method has shown responses in patients with bone sarcomas. In particular treatment with this method has shown responses in patients with gastrointestinal stromal sarcomas. In particular treatment with this method has shown responses in patients with breast cancers.

The table, FIG. 1, shows responses observed with this method of treatment.

The invention is further illustrated by the following examples which relate to clinical trials in humans.

EXAMPLE 1

Data was analyzed from trials with 24 h iv continuous infusion of ET 743 every 3 or 4 weeks at 1500 g/$\mu$m$^2$.

Pharmacokinetics of ET-743 are monitored in all patients during the first cycle of therapy to assess interpatient variability and possible correlations with clinical activity or toxicity
Patient Population:
16 advanced/metastatic soft tissue sarcoma (STS) patients
12 soft tissue sarcoma patients with no prior chemotherapy treatments
8 advanced/metastatic gastrointestinal stromal tumor (GIST) patients.
Safety/Toxicities Observed:
Tolerabilty of treatment was very good.
Nausea essentially eliminated by use of dexamethasone as a prophylactic anti emetic
Myelosuppression
Temporary/asymptomatic transaminitis
Fatigue
Data showed no significant differences with early phase I data
Efficacy 6 out of 10 evaluable STS patients without any prior chemotherapy treatment have exhibited stable disease or minor responses after 2 cycles of therapy, 4 out of 12 evaluable STS patients with prior chemotherapy treatment have exhibited stable disease or minor responses after 2 cycles of therapy, preliminary evidence of activity was observed in liposarcoma, leiomyo sarcoma, and synovial sarcoma.

EXAMPLE 2

Data was analyzed from a trial with 24 h iv continues infusion of ET 743 every 3 weeks on 20 pretreated advanced/metastatic breast cancer patients, at a dose level of 1500 µg/m².

Characteristics of Patient Population:
20 women,
all presenting measurable disease and progressing at study entry age 33 to 64 years (median 50 yrs)
performance status 0-1 (ECOG criteria)
minimum number of involved organs: 2 (range 1-6)
Disease Sites:

|  |  |
| --- | --- |
| cutaneous | 12 (60%) |
| liver | 10 (50%) |
| bone | 9 (45%) |
| lymph nodes | 6 (30%) |
| pleuro pulmonary | 6 (30%) |

|  |  |
| --- | --- |
| Minimum number of prior chemotherapy treatments | 2 (1-6) |
| Patients previously treated with Anthracyclines | 20 |
| Patients previously treated with Taxanes | 16 |
| Patients resistant to Anthracyclines and Taxanes | 5 |
| Patients resistant to Taxanes only | 2 |
| Patients resistant to Anthracyclines only | 3 |

Safety/Toxicities:

|  |  |
| --- | --- |
| Total number of cycles administered | 56 |
| minimum number of cycles per patient | 2 (range 1-8) |
| Number of grade | 3 or 4 toxicities reported per cycle. |
| Neutropenia | 25 (50%) |
| Thrombocytopenia | 4 (2%) |
| Reversible transaminitis | 34 (60%) |
| Asthenia (grade 2/3) | 13 (23%) |

Data showed no significant differences with early phase I data
Efficacy

On 16 evaluable patients, Two partial responses were observed (pleuropulmonary and thoracic skin involvement) lasting 3.5 and over 2 months on patients without primary resistance to either pretreatment drug. Six patients achieved disease stabilization (over 2, 3, 3, over 3, 4.5 and over 6 months) including two with sustained decrease in CA 15-3 a marker for this disease.

EXAMPLE 3

Data was analyzed from a trial with 24 h iv continues infusion of ET 743 every 3 weeks on 20 pretreated advanced/metastatic soft tissue sarcoma patients, with all except two patients being treated at a dose level of 1500 µg/m²

Characteristics of Patient Population:
39 patients/22 female
35 Soft tissue sarcoma (STS)
3 osteosarcoma (OS)
1 Ewing sarcoma (ES)
22 patients had bulky disease at study entry, with 56% of disease progression under prior regime
age 16 to 71 years (median 45 yrs)
performance status 0 (0-2) (ECOG criteria)
Minimum number of prior chemotherapy treatments 2 (1-7)
Most patients had received as prior chemotherapy treatments Anthracyclines and alkylators
Safety/Toxicities:

|  |  |
| --- | --- |
| Total number of cycles administered | 137 |
| minimum number of cycles per patient | 2 (range 1-12) |
| Number of grade | 3 or 4 toxicities reported per cycle. |
| Neutropenia | 34%, with 6.5% febrile |
| Thrombocytopenia | 5% |
| Acute, reversible transaminitis | 44% |
| Asthenia (grade 2/3) | 13 (23%) |

Data showed no significant differences with early phase I data
Efficacy

On 34 evaluable patients,
4 partial responses (11.7%) were observed, two of which became post surgical complete response
3 minor responses were observed, one of which became post surgical complete response 11 disease stabilizations, most of which lasting 3 months or more Responses were observed in various histological types, including 2 out of 3 osteo sarcomas, in all disease sites, including visceral metastases, in bulky and non bulky disease, and in anthracycline refractory and non refractory tumours.

The sc B 16 tumor model in male rats was used to compare dexamethasone pre-treated (3 mg/kg total dose; −15 min.), ET743 (90 µg/kg TD) animals to ET alone on a q2dx5, iv, schedule. Preliminary results on Day 14 show significant activity in the DEX-ET combination animals compared to ET alone. The following table gives the tumor volumes relative to controls and the BW indicating no significant toxicity with this combination.

| Group | Dose | Schedule | Vol. (mm³) | BW (grams) |
| --- | --- | --- | --- | --- |
| Vehicle | — | q2dx5 | 18,862 | 216 |
| DEX | 0.60 mg/kg | q2dx5 | 17,252 | 217 |
| ET | 0.018 mg/kg | q2dx5 | 15,243 | 198 |
| DEX/ET | 0.60 mg/kg (−24 hrs) DEX +0.018 mg/kg ET | q2dx5 | 6,653 | 170 |

The invention claimed is:

1. A method of treating a cancer selected from sarcoma, breast cancer, ovarian cancer, and melanoma in a human patient in need thereof by combination therapy comprising administration of ecteinascidin-743 (Et 743) and dexamethasone to said patient, wherein said administration leads to a reduction in tumor size compared to administration of the Et 743 alone.

2. The method of claim 1, wherein dexamethasone and Et 743 are administered as a single medicament.

3. The method of claim 1, wherein dexamethasone is administered as a separate medicament.

4. The method of claim 3, wherein the separate dexamethasone medicament is administered at the same time as Et 743.

5. The method of claim 3, wherein the separate dexamethasone medicament is administered at a different time as Et 743.

6. The method according to any one of claims 1 to 5, wherein the patient has advanced and/or metastatic, previously treated cancer.

7. The method according to any one of claims 1 to 5, wherein the patient has cancer resistant or refractory to other treatments.

8. The method according to any one of claims 1 to 5, wherein the patient has a sarcoma.

9. The method according to claim 7, wherein the patient has a soft tissue sarcoma.

10. The method according to claim 7, wherein the patient has a bone sarcoma.

11. The method according to any one of claims 1 to 5, wherein the patient has breast cancer.

12. The method according to any one of claims 1 to 5, wherein the patient has ovarian cancer.

13. The method according to any one of claims 1 to 5, wherein the patient has melanoma.

\* \* \* \* \*